(12) United States Patent
Li et al.

(10) Patent No.: US 8,871,080 B2
(45) Date of Patent: Oct. 28, 2014

(54) MANAGEMENT SYSTEM FOR AN ELECTROLYTE ANALYZER

(75) Inventors: Qing Li, Hitachinaka (JP); Tomonori Mimura, Kasama (JP); Shinichi Fukuzono, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 210 days.

(21) Appl. No.: 13/514,187

(22) PCT Filed: Nov. 10, 2010

(86) PCT No.: PCT/JP2010/006576
§ 371 (c)(1),
(2), (4) Date: Jun. 26, 2012

(87) PCT Pub. No.: WO2011/070719
PCT Pub. Date: Jun. 16, 2011

(65) Prior Publication Data
US 2012/0261260 A1 Oct. 18, 2012

(30) Foreign Application Priority Data
Dec. 8, 2009 (JP) ................................ 2009-278106

(51) Int. Cl.
*G01N 27/333* (2006.01)
(52) U.S. Cl.
CPC .................................. *G01N 27/333* (2013.01)
USPC ............................ 205/789; 204/416; 73/1.03
(58) Field of Classification Search
CPC ........................... G01N 27/333; G01N 27/416
USPC .................... 204/400–419; 205/789; 73/1.03
See application file for complete search history.

(56) References Cited

U.S. PATENT DOCUMENTS

| 5,288,374 | A  | * | 2/1994  | Watanabe et al. | 205/779    |
| 6,464,848 | B1 | * | 10/2002 | Matsumoto       | 204/403.06 |
| 2004/0262170 | A1 | * | 12/2004 | Centanni     | 205/782    |
| 2010/0219074 | A1 | * | 9/2010  | Ishibe        | 204/406    |

FOREIGN PATENT DOCUMENTS

| CN | 101855544 A    |   | 10/2010 |
| EP | 1 906 179      | * | 4/2008  |
| EP | 1906179 A1     |   | 4/2008  |
| EP | 2048495 A1     |   | 4/2009  |
| EP | 2208989 A1     |   | 7/2010  |
| JP | 08-035944 A    |   | 2/1996  |
| JP | 2001-004586 A  |   | 1/2001  |
| WO | 2009060727 A1  |   | 5/2009  |
| WO | WO 2009/060727 | * | 5/2009  |

OTHER PUBLICATIONS

Chinese Office Action received in Chinese Application No. 201080055376.2 dated Nov. 22, 2013.

* cited by examiner

*Primary Examiner* — Jennifer Dieterle
(74) *Attorney, Agent, or Firm* — Mattingly & Malur, PC

(57) ABSTRACT

Electrolyte analyzers are used in a variety of ways, and problems vary from reagent deterioration due to reagent replenishment, mixing of foreign substances during reagent replenishment, electrode deterioration due to the passage of the validity date, to the operator's inputting errors. It is thus necessary to judge abnormalities of measured values resulting from such inappropriate usage, based on the fluctuation patterns of the results of daily electrolyte calibration. The fluctuation patterns of each measured item are extracted from the results of daily electrolyte calibration. The electromotive force balance ratio between the internal standard solution and high/low-concentration standard solutions is calculated as well as its fluctuation pattern. The obtained fluctuation patterns are compared against atypical fluctuation patterns stored in the electrolyte analyzer. When any of the extracted patterns matches any of the atypical patterns, the analyzer activates an alarm.

8 Claims, 6 Drawing Sheets

MANAGEMENT SYSTEM FOR AN ELECTROLYTE ANALYZER

TECHNICAL FIELD

The present invention relates to electrolyte analyzers for examining the icon components contained in a biological sample (e.g., blood, urine, etc.) and particularly to an electrolyte analyzer with a mechanism for detecting abnormalities of the analyzer.

BACKGROUND ART

Electrolyte analyzers are used to analyze the ion components (e.g., sodium, potassium, chlorine, etc.) contained in a biological sample (e.g., blood, urine, etc.). At present, the most frequently used electrolyte analyzers are those involving the use of ion-selective electrodes to measure particular ions in a sample. Such electrolyte analyzers are designed to measure standard solutions of known concentrations in advance to obtain electromotive forces and calculate slopes using the obtained electromotive forces. Such analyzers further measure an internal standard solution and a sample in an alternate manner to obtain their potential difference, thereby measuring the concentrations of particular ions in the sample based on the potential difference. The electrolyte analyzers disclosed in Patent Documents 1 and 2 are examples of the above analyzers.

When ion-selective electrodes are used, a diluent is used to dilute a sample at a particular ratio, and the diluted sample is subjected to measurement. Thus, deterioration of the diluent or mixing of foreign substances into the diluent may result in abnormal measurement data of standard solutions. Because this often occurs after reagent replenishment, it is recommended that, before measurement of a sample, calibration be conducted without reagent replenishment, using new reagents and standard solutions each time.

PRIOR ART DOCUMENTS

Patent Documents

Patent Document 1: JP-1996-35944-A
Patent Document 2: JP-2001-4586-A

SUMMARY OF THE INVENTION

Problems to be Solved by the Invention

In fact, electrolyte analyzers involving the use of ion-selective electrodes are used in a variety of ways, and reagent replenishment is often conducted though this is not allowed by manuals for electrolyte analyzers. Also, reagents may be used even after the expiration of their validity dates, or a reagent may be left untreated for a long period of time after opening, resulting in the deterioration of the reagent due to falling bacteria. If a diluent under such a condition is used to dilute a sample of known concentration at a particular ratio, followed by measurement of the diluted sample, it is necessary to examine whether the gradually deteriorating diluent is exerting influence on the measurement or not. To do so requires the operator to check all the results of calibration in which the sample of the known concentration was used, and this is a considerably time-consuming task. In addition, there are also between-day variations in which a reagent deteriorates gradually. Thus, years of experience and expertise are required not to miss even a hard-to-detect slight fluctuation.

During reagent replenishment, the operator may occasionally use the wrong reagent, producing abnormal sample measurement results. To find out the causes of the abnormalities, the operator must check the measurement process again, measure the sample of known concentration several times, and verify the reproducibility of the measurement results and the details of calibration results. Thus, a great deal of difficulty is involved in handling electrolyte analyzers.

Furthermore, while an electrode has an expiration date and an upper limit on the number of uses, it may occasionally be used for measurement even past such a limit. The use of an electrode that has passed its expiration date makes it difficult to detect gradually changing selectivity and changes in electromotive force.

An object of the present invention is to provide an electrolyte analyzer that, for the purpose of enhancing the reliability of measurement data, readily examines the deterioration of a reagent due to the passage of its validity date or replenishment as well as the deterioration of electrodes due to the passage of their expiration dates, based on the results of daily calibration in which samples of known concentrations are used.

Means for Solving the Problems

To address the above issues, an electrolyte analyzer of the present invention performs the following operations:

(1) The electrolyte analyzer, which includes ion-selective electrodes to measure the concentrations of particular ions in a sample, first stores the results of calibration in which the sample of known concentration is measured and then extracts fluctuation patterns that occur with the passage of time. Examples of such fluctuation patterns include the fluctuation patterns of: slope values; the concentration and electromotive force of an internal standard solution; the electromotive forces of high/low-concentration standard solutions; and the electromotive force of a calibrator, all of which can be obtained from the calibration results.

(2) The analyzer computes a balance ratio using the electromotive force of the internal standard solution and the electromotive forces of the high/low-concentration standard solutions, thereby extracting the fluctuation pattern of the balance ratio that occur with the passage of time.

(3) The analyzer compares the fluctuation patterns of the calibration results and the fluctuation patterns of the electromotive force balance ratio against atypical fluctuation patterns stored on the analyzer to examine deterioration of the ion-selective electrodes, deterioration of reagents, mixing of foreign substances into the reagents, and errors in inputting the concentrations of the standard solutions.

The deterioration of the electrodes and the reagents can be examined with ease based on the fluctuation patterns of the results of calibration in which the sample of known concentration was used.

Effects of the Invention

In accordance with the invention, it is possible to utilize the results of daily calibration in which a sample of known concentration is used and easily examine the deterioration of regents and electrodes used in an electrolyte analyzer involving the use of ion-selective electrodes, mixing of foreign substances into the reagents, and human setting errors. It is also possible to detect problems before they get serious, whereby the reliability of measurement data can be enhanced.

MODE FOR CARRYING OUT THE INVENTION

The present invention provides a management system for an electrolyte analyzer that involves the use of ion-selective electrodes to measure patient samples (e.g., blood, urine, etc.) in a clinical assay. The system performs the following operations: extracting the characteristics of fluctuation from multiple fluctuation patterns of the results of calibration in which a sample of known concentration was measured; calculating an electromotive force balance ratio from the electromotive forces of an internal standard solution and high/low-concentration standard solutions; comparing the fluctuation pattern of the balance ratio and the fluctuation patterns of the calibration results against atypical fluctuation patterns stored on the analyzer; examining the deterioration of the electrodes and a reagent, the mixing of foreign substances into the reagent, and errors in inputting the concentrations of the standard solutions; and activating an alarm.

Note that, according to the invention, "the results of electrolyte calibration in which standard solutions of known concentrations were measured" include the following: slope, the measured concentration of the internal standard solution, correction coefficients, the measured electromotive force of the internal standard solution, the electromotive force of the low-concentration standard solution, the electromotive force of the high-concentration standard solution, and the measured electromotive force of a calibrator.

Note also that, according to the invention, "fluctuation patterns" are the shift and drift patterns of each measured item of the results of electromotive force calibration; and the shift and drift patterns of the electromotive force balance ratio calculated from the electromotive force of the internal standard solution and from the electromotive forces of the high/low-concentration standard solutions.

The present invention will now be described in detail with specific examples.

Figure 1:
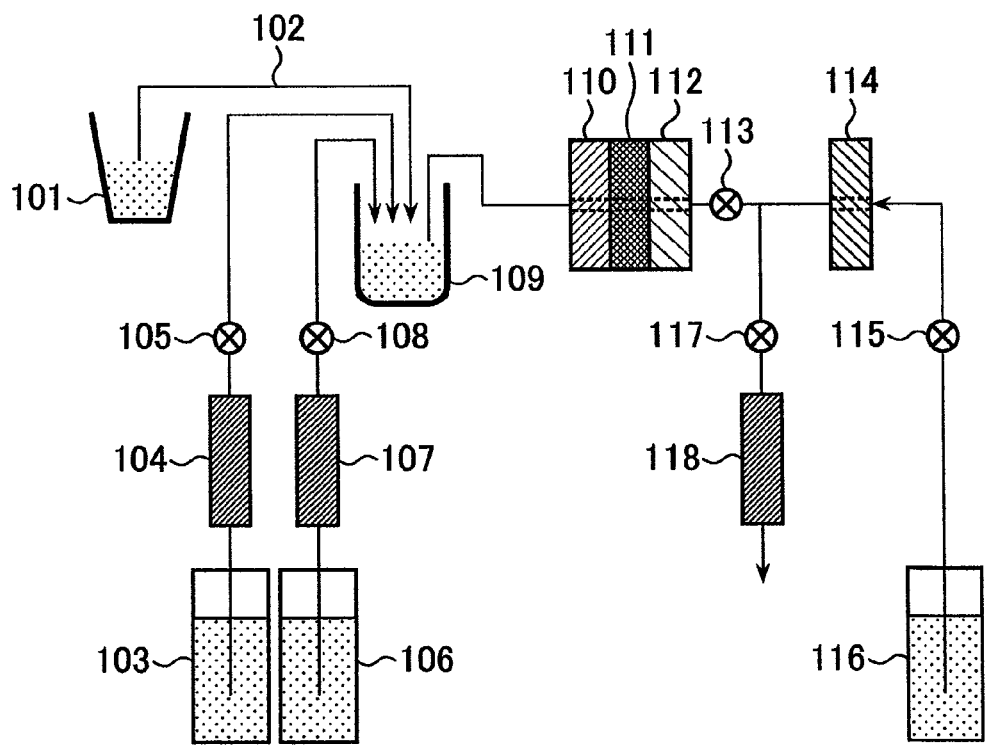
FIG. 1 is a schematic illustrating the configuration of an electrolyte analyzer with ion-selective electrodes.

FIG. 1 is a schematic illustrating the configuration of an electrolyte analyzer according to the invention, which includes ion-selective electrodes. First described with reference to FIG. 1 is the operation of the electrolyte analyzer. As illustrated in FIG. 1, a sample dispensing nozzle 102 suctions a particular amount of a sample from a sample vessel 101 and discharges the sample into a dilution tank 109. The operation of a diluent syringe 104 and a solenoid valve 105 for diluent then causes a diluent to transfer from a diluent bottle 103 to the dilution tank 109, thereby diluting the sample which has been discharged from the sample vessel 101 to the dilution tank 109.

Next, the operation of a sipper syringe 118, a solenoid valve 117 for shipper, and a pinch valve 113 causes the diluted sample to be suctioned from the dilution tank 109 into a sodium ion selective electrode 110, a potassium ion selective electrode 111, and a chlorine ion selective electrode 112. In the meantime, a solenoid valve 115, the sipper syringe 118, and the solenoid valve 117 operate together to suction an electrode solution from an electrode solution bottle 116 into a comparative electrode 114, thereby conducting electromotive force correction.

Thereafter, a solenoid valve 108 for internal standard solution and an internal standard solution syringe 107 operate together to transfer an internal standard solution from an internal standard solution bottle 106 to the dilution tank 109. This is followed by the alternate transfer of the diluted sample and the internal standard solution into the ion-selective electrodes 110, 112, and 113 and by the measurement of the electromotive forces of the sample and the internal standard solution. With calibration using standard solutions of known concentrations, slope sensitivity, as well as the electromotive forces of the internal standard solution and the sample of known concentration, is obtained. The concentrations of the internal standard solution and the sample are computed from their potential difference.

The concentration of the sample and the balance ratio of the electromotive forces are calculated using the following equations.

(1) Calculation of the Slope Sensitivity (Based on Calibration Using Standard Solutions of Known High/Low Concentrations)

$$SL = (EMF_H - EMF_L)/(Log C_H - \text{Log(Chlorine ions)}) \quad (1)$$

SL: Slope sensitivity $EMF_H$: The measured electromotive force of the standard solution of the known high concentration $EMF_L$: The measured electromotive force of the standard solution of the known low concentration $C_H$: The known concentration of the high-concentration standard solution Chlorine ions: The known concentration of the low-concentration standard solution (2) Calculation of the Internal Standard Solution Concentration $$C_{IS} = \text{Chlorine ions} \times 10^a \quad (2)$$

$$a = (EMF_{IS} - EMF_L)/SL \quad (3)$$

$C_{IS}$: The concentration of the internal standard solution $EMF_{IS}$: The electromotive force of the internal standard solution (3) Calculation of the Sample Concentration $$C_S = C_{IS} \times 10^b \quad (4)$$

$$b = (EMF_{IS} - EMF_S)/SL \quad (5)$$

Cs: The concentration of the sample $EMF_S$: The measured electromotive force of the sample (4) Calculation of the Balance Ratio of the Electromotive Forces $$\text{Balance Ratio} = (EMF_H - EMF_{IS})/(EMF_{IS} - EMF_L) \quad (6)$$

Figure 2:
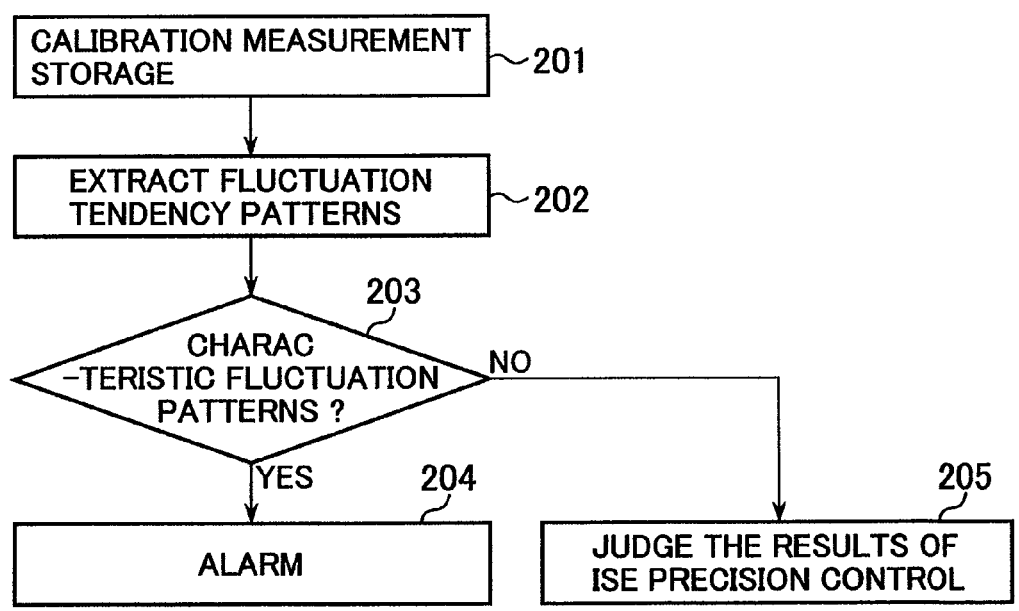
FIG. 2 is an operational flowchart according to an embodiment of the invention.

The flowchart of FIG. 2 describes the operation of the analyzer according to a first embodiment of the invention. This first embodiment is based on the assumption that a sample of known concentration is used during calibration.

After the calibration measurement and measurement data storage (Step 201), the electrolyte analyzer extracts fluctuation patterns for each relevant item in an automatic fashion (Step 202). The analyzer then compares the extracted fluctuation patterns against atypical fluctuation patterns (stored on the analyzer in advance) as in Step 203. When any of the extracted patterns matches any of the atypical patterns, the analyzer activates an alarm (Step 204). If not, the process proceeds to Step 205 in which the results of the electrolyte precision control are judged.

Figure 3:
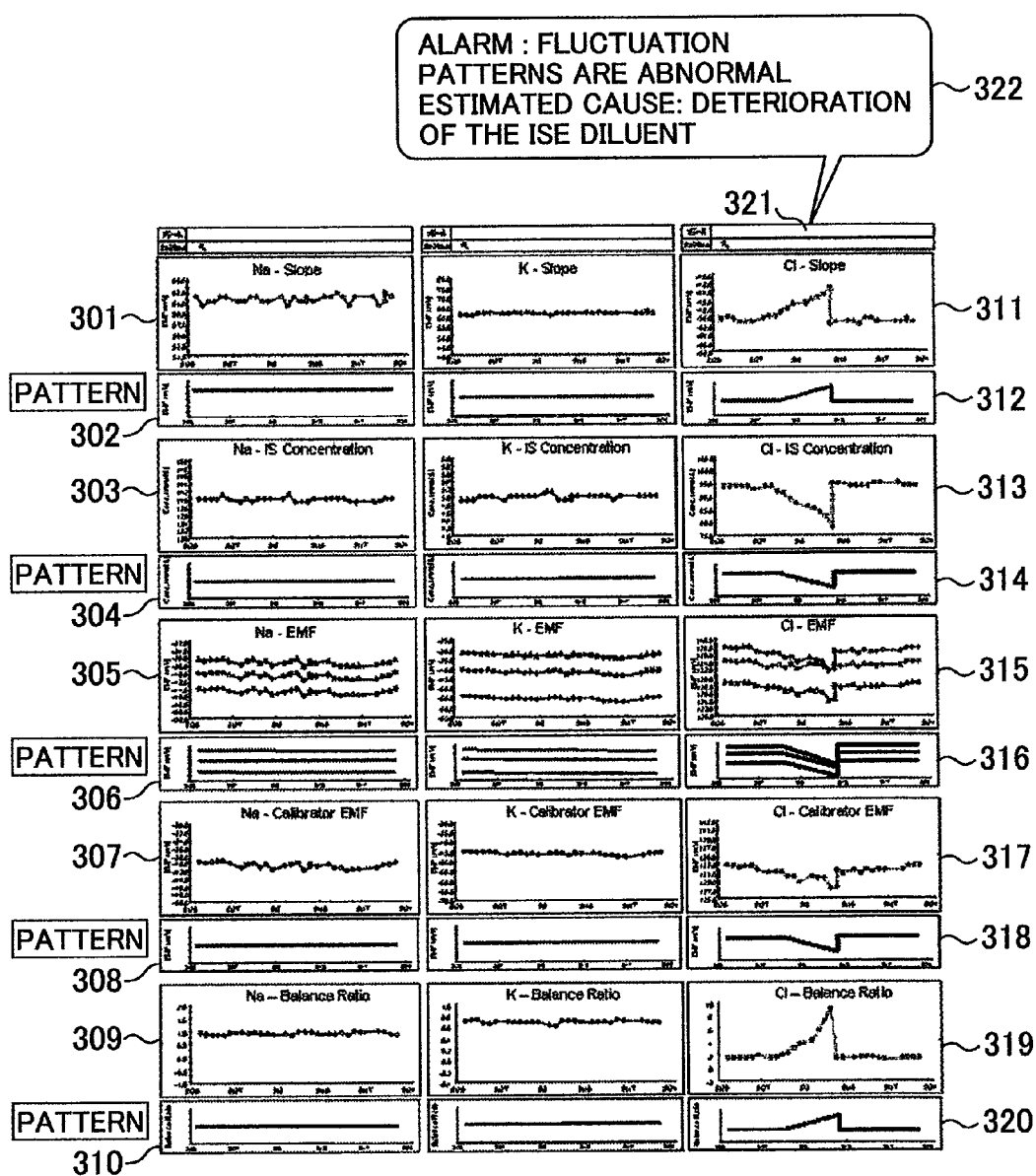
FIG. 3 illustrates fluctuation patterns of electrolyte calibration resulting from diluent deterioration.

FIG. 3 is an example of a monitor screen with which to control deterioration of a diluent based on a method of control of measured values according to the invention.

As illustrated in FIG. 3, the screen displays the results of a month's electrolyte calibration, together with extracted fluctuation patterns for each item. Specifically, the screen shows the following: slope 301 and its fluctuation pattern 302; the measured concentration 303 of the internal standard solution and its fluctuation pattern 304; the electromotive forces 305 of the internal standard solution and standard solutions of high/low concentrations and their fluctuation patterns 306; the electromotive force 307 of the calibrator and its fluctuation pattern 308; and the balance ratio 309 of the electromotive forces and its fluctuation pattern 310. As can be seen, only the chlorine ion section exhibited signs of fluctuation (i.e., drift and shift patterns). Note that in the section of the electromotive forces 305 of the internal standard solution and high/low-concentration standard solutions, the triangular, square, and circular marks represent respectively the electromotive forces of the high-concentration standard solution, the low-concentration standard solution, and the internal standard solution. The color and shape of those marks and other lines in FIG. 3, however, are only meant to be an example and not limited to such representation.

While the electromotive forces are stable in the sections of sodium and potassium ions, the chlorine section exhibited drift patterns in the fluctuation patterns 316 of the electromotive forces 315 of the internal standard solution and high/low-concentration standard solutions as well as in the fluctuation pattern 318 of the electromotive force 317 of the calibrator. Because similar drift patterns can be found in the slope fluctuation pattern 312 and the electromotive force balance ratio 318 of the chlorine ion section, those abnormal patterns can be attributed to the diluent. Possibly, they may have been caused by the expiration of the diluent validity date or by deterioration due to several reagent replenishments. Accordingly, an alert icon 321 is displayed on the screen. The operator can click on the alert icon 321 to see an alarm 322 (including the estimated causes).

Figure 4:
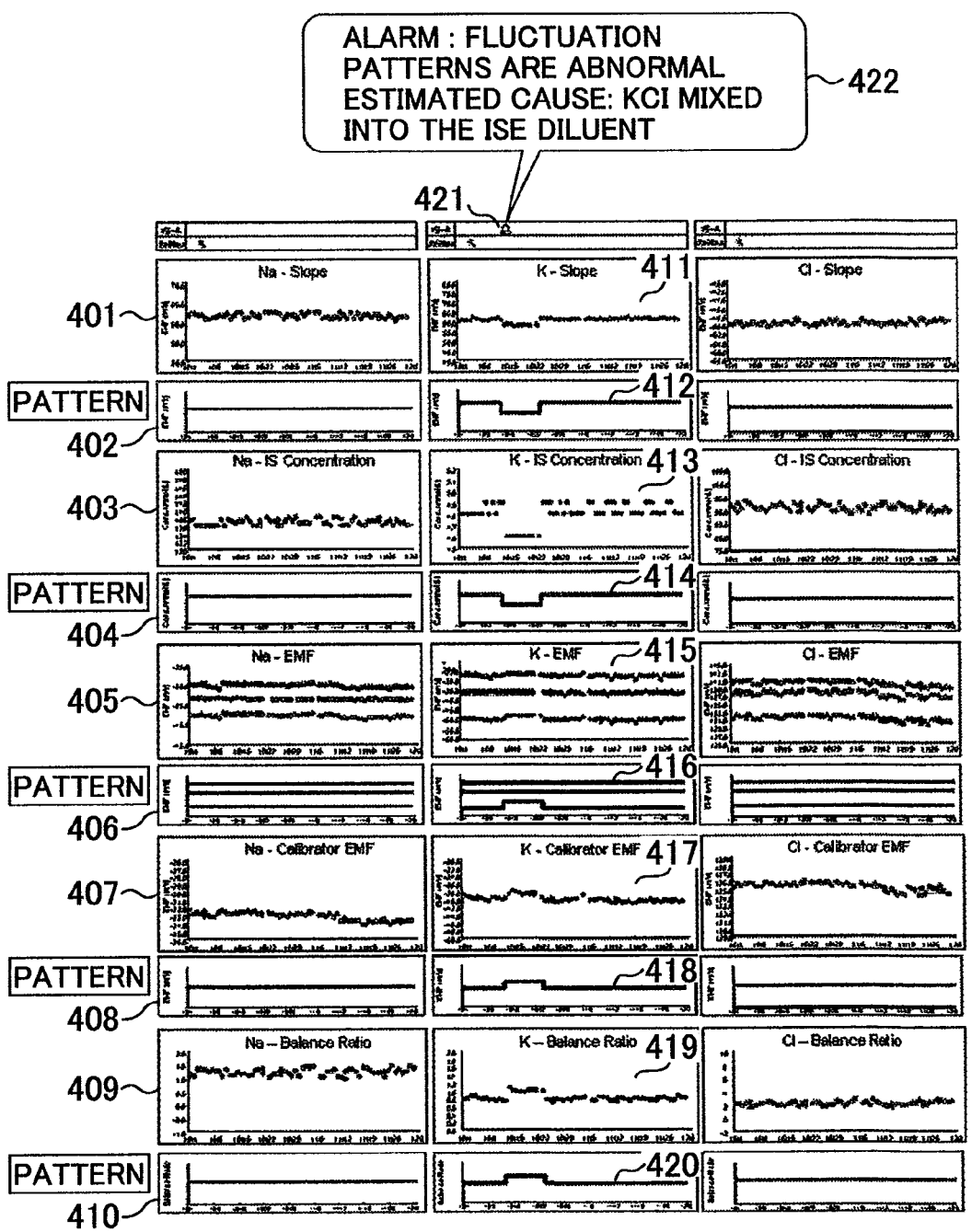
FIG. 4 illustrates fluctuation patterns of electrolyte calibration resulting from mixing of foreign substances into a diluent.

FIG. 4 is an example of a monitor screen with which to prevent potassium ions from being mixed into the diluent based on a method of control of measured values according to the invention.

As illustrated in FIG. 4, the screen displays the results of two months' electrolyte calibration, together with extracted fluctuation patterns for each item. Specifically, the screen shows the following: slope 401 and its fluctuation pattern 402; the measured concentration 403 of the internal standard solution and its fluctuation pattern 404; the electromotive forces 405 of the internal standard solution and standard solutions of high/low concentrations and their fluctuation patterns 406; the electromotive force 407 of the calibrator and its fluctuation pattern 408; and the balance ratio 409 of the electromotive forces and its fluctuation pattern 410. As can be seen, only the potassium ion section exhibited signs of fluctuation (i.e., shift patterns). Note that in the section of the electromotive forces 305 of the internal standard solution and high/low-concentration standard solutions, the triangular, square, and circular marks represent respectively the electromotive forces of the high-concentration standard solution, the low-concentration standard solution, and the internal standard solution. The background color, line colors, and mark shapes in FIG. 4, however, are only meant to be an example and not limited to such representation.

In the section of potassium ions, while the electromotive forces 315 of the internal standard solution and the high-concentration standard solution are stable, the electromotive force of the low-concentration standard solution exhibited an upward shift, so did the fluctuation pattern 318 of the calibrator electromotive force 317 and the fluctuation pattern 420 of the electromotive force balance ratio 419. On the other hand, the calibration results of sodium and chlorine ions are all stable. It is thus likely that potassium icons may have been mixed into the diluent for some reason. Accordingly, an alert icon 421 is displayed on the screen. The operator can click on the alert icon 421 to see an alarm 422 (including the estimated cause).

Figure 5:
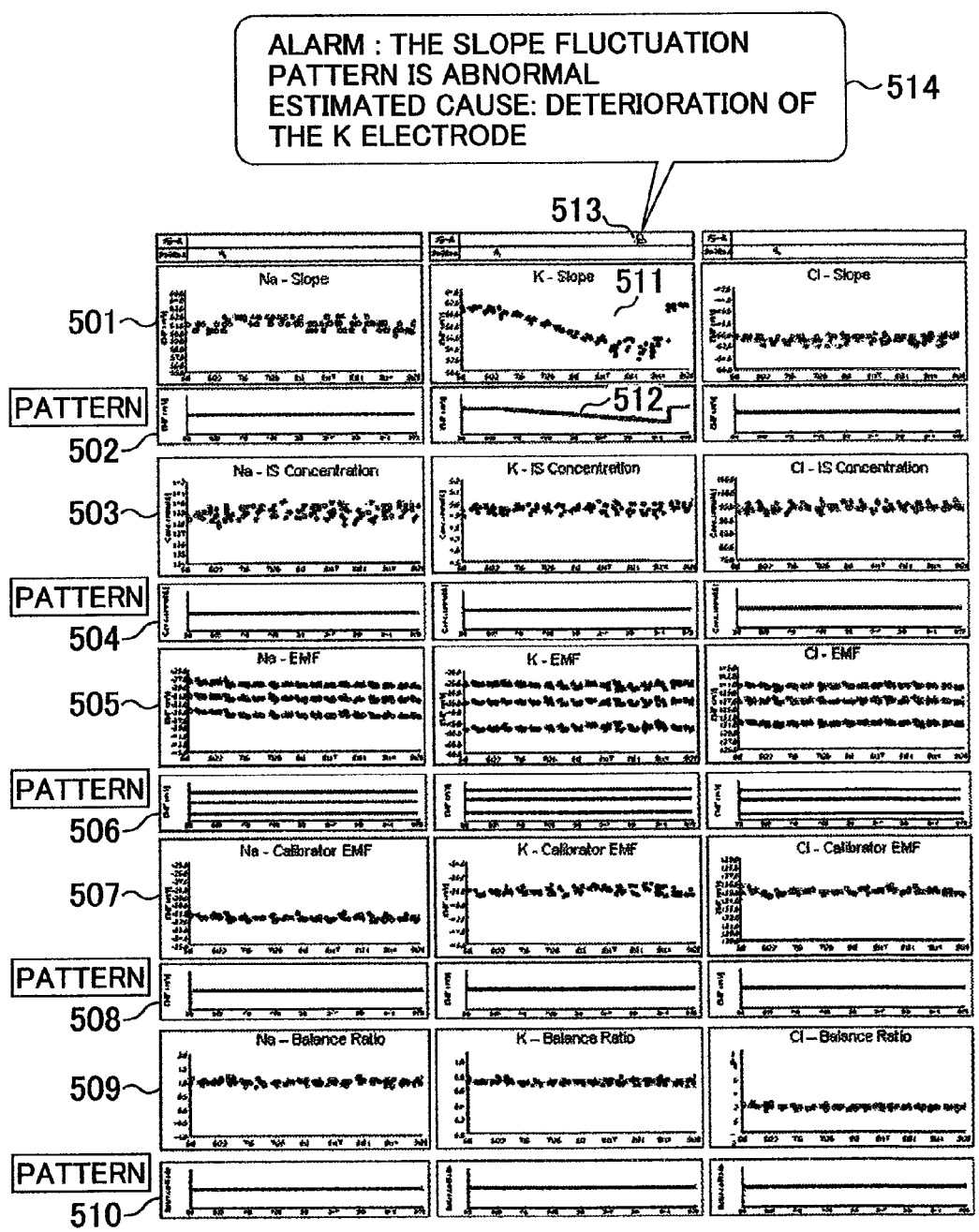
FIG. 5 illustrates fluctuation patterns of electrolyte calibration resulting from deterioration of an ion-selective electrode.

FIG. 5 is an example of a monitor screen with which to prevent deterioration of the ion-selective electrodes based on a method of control of measured values according to the invention.

As illustrated in FIG. 5, the screen displays the results of three months' electrolyte calibration, together with extracted fluctuation patterns for each item. Specifically, the screen shows the following: slope 501 and its fluctuation pattern 502; the measured concentration 503 of the internal standard solution and its fluctuation pattern 504; the electromotive forces 505 of the internal standard solution and standard solutions of high/low concentrations and their fluctuation patterns 506; the electromotive force 507 of the calibrator and its fluctuation pattern 508; and the balance ratio 509 of the electromotive forces and its fluctuation pattern 510.

As can be seen, only the fluctuation pattern 512 of the slope 511 in the potassium ion section exhibited a downward drift. All the other measured items for potassium icons (including the balance ratio 509) are stable, so are the calibration results of sodium and chlorine ions. Therefore, the abnormal fluctuation can be attributed to the deterioration of the potassium ion selective electrode. Possibly, the validity date of the electrode may have expired. Accordingly, an alert icon 513 is displayed on the screen. The operator can click on the alert icon 513 to see an alarm 514 (including the estimated cause).

Figure 6:
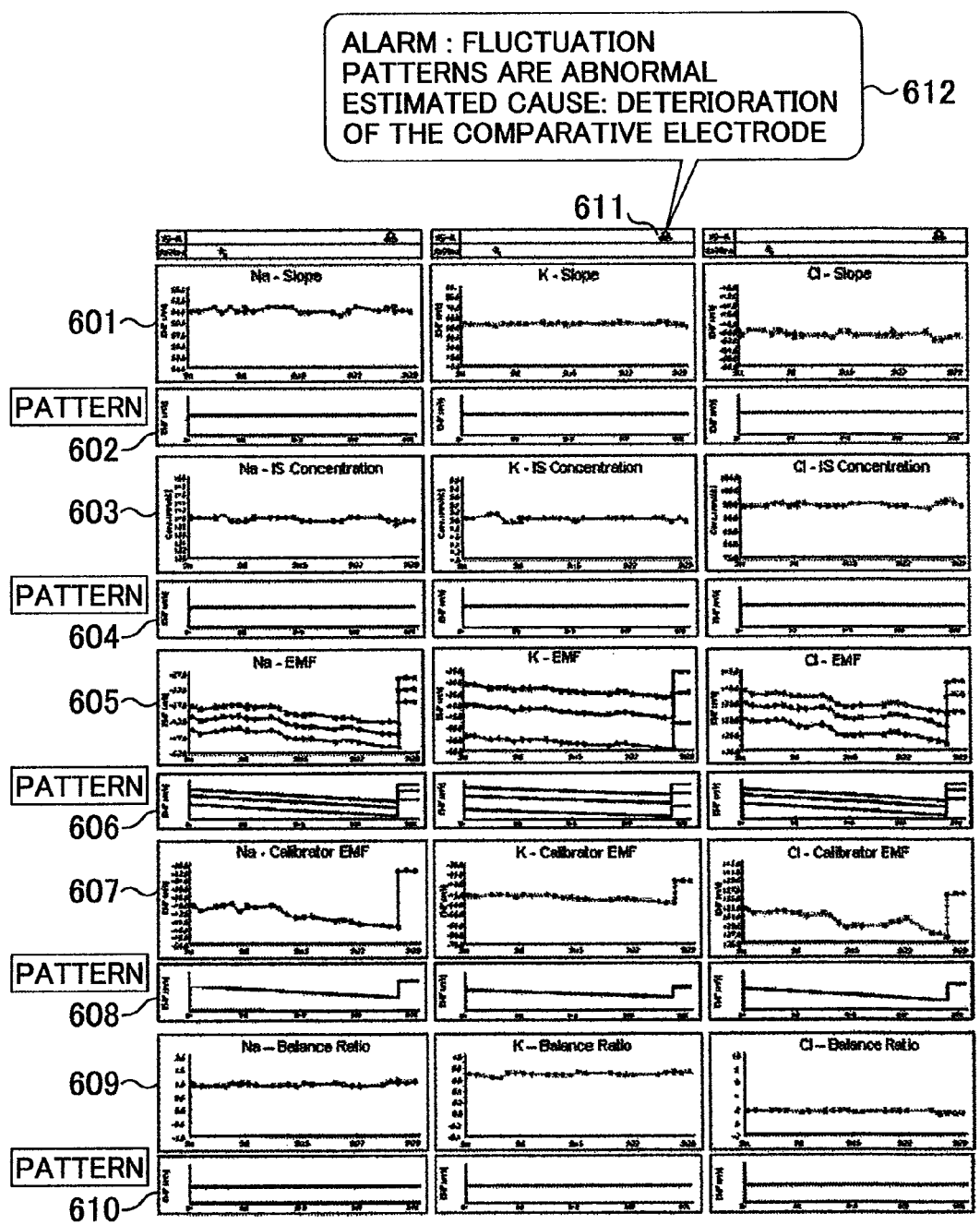
FIG. 6 illustrates fluctuation patterns of electrolyte calibration resulting from deterioration of a comparative electrode.

FIG. 6 is an example of a monitor screen with which to prevent deterioration of the comparative electrode based on a method of control of measured values according to the invention.

As illustrated in FIG. 6, the screen displays the results of a month's electrolyte calibration, together with extracted fluctuation patterns for each item. Specifically, the screen shows the following: slope 601 and its fluctuation pattern 602; the measured concentration 603 of the internal standard solution and its fluctuation pattern 604; the electromotive forces 605 of the internal standard solution and standard solutions of high/low concentrations and their fluctuation patterns 606; the electromotive force 607 of the calibrator and its fluctuation pattern 608; and the balance ratio 609 of the electromotive forces and its fluctuation pattern 610.

As can be seen, the slope fluctuation pattern 602, the fluctuation pattern 604 of the internal standard solution concentration, and the balance ratio fluctuation pattern 610 are all stable. However, all the three sections of sodium, potassium, and chlorine ions exhibited downward drifts in the fluctuation patterns 606 of the standard solution electromotive forces 605 as well as in the fluctuation patterns 608 of the calibrator electromotive forces 607. These electromotive force decreases can be attributed to the deterioration of the comparative electrode which was used for the calibration for sodium, potassium, and chlorine ions. Accordingly, an alert icon 611 is displayed on the screen. The operator can click on the alert icon 611 to see an alarm 612 (including the estimated cause).

Figure 7:
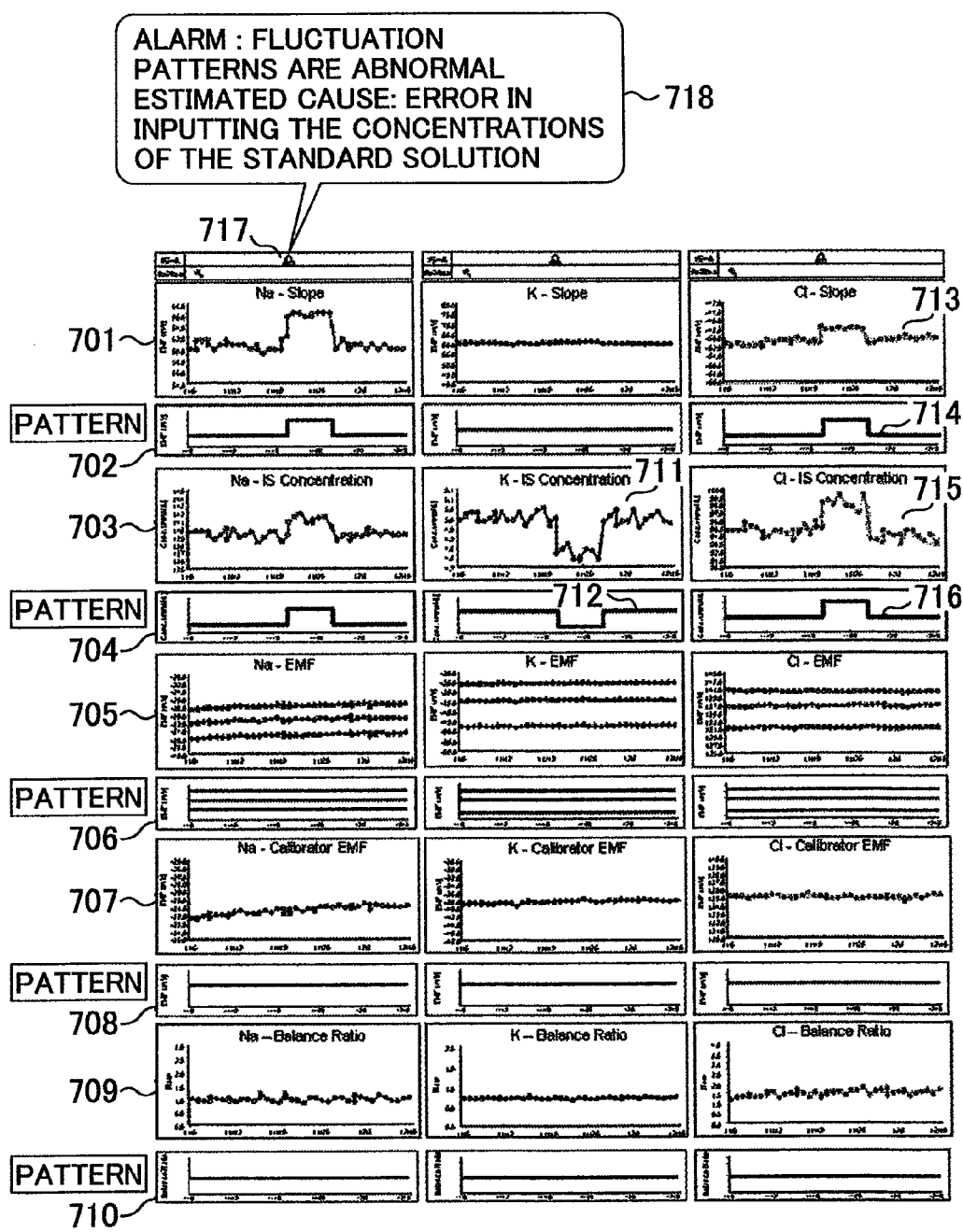
FIG. 7 illustrates fluctuation patterns of electrolyte calibration resulting from an error in inputting the concentrations of standard solutions.

FIG. 7 is an example of a monitor screen with which to manage input values for standard solution concentrations based on a method of control of measured values according to the invention.

As illustrated in FIG. 7, the screen displays the results of a month's electrolyte calibration, together with extracted fluctuation patterns for each item. Specifically, the screen shows the following: slope 701 and its fluctuation pattern 702; the measured concentration 703 of the internal standard solution and its fluctuation pattern 704; the electromotive forces 705 of the internal standard solution and standard solutions of high/low concentrations and their fluctuation patterns 706; the electromotive force 707 of the calibrator and its fluctuation pattern 708; and the balance ratio 709 of the electromotive forces and its fluctuation pattern 710.

As can be seen, the electromotive forces 705 of the internal standard solution and the high/low-concentration standard solutions and the electromotive force 707 of the calibrator are stable. However, upward shifts are found in the slope fluctuation pattern 702 and the fluctuation pattern 704 of the internal standard solution concentration in the sodium ion section as well as in the slope fluctuation pattern 714 and the fluctuation pattern 716 of the internal standard solution concentration in the chlorine ion section. Also, in the potassium ion section, the fluctuation pattern 712 of the internal standard solution concentration 711 exhibited a downward shift while the slope of potassium ions is stable. Because the slopes of sodium, potassium, chlorine icons and their respective internal standard solution concentrations are calculated with the use of electromotive forces, those shifts in slope and internal standard solution concentration, regardless of the stable electromotive forces, can be attributed to an error in inputting the concentrations of the standard solutions. Accordingly, an alert icon 717 is displayed on the screen. The operator can click on the alert icon 717 to see an alarm 718 (including the estimated cause).

DESCRIPTION OF THE REFERENCE NUMERALS

101: Sample vessel
102: Sample dispensing nozzle
103: Diluent bottle
104: Diluent syringe
105: Solenoid valve for diluent
106: Internal standard solution bottle
107: Internal standard solution syringe
108: Solenoid valve for internal standard solution
109: Dilution tank
110: Sodium ion selective electrode
111: Potassium ion selective electrode
112: Chlorine ion selective electrode
113: Pinch valve
114: Comparative electrode
115: Solenoid valve for comparative electrode
116: Electrode solution bottle
117: Solenoid valve for sipper
118: Sipper syringe

The invention claimed is:

1. A management method for an electrolyte analyzer, the method comprising:
   measuring concentrations of particular ions in a sample with ion-selective electrodes; and
   calculating a balance ratio of electromotive forces from an electromotive force of an internal standard solution, an electromotive force of a high-concentration standard solution and an electromotive force of a low-concentration standard solution, all the electromotive forces being obtained from calibration in which a sample of known concentration was measured,
   wherein the balance ratio is calculated from the following equation:
   {(the electromotive force of the high-concentration standard solution)−(the electromotive force of the internal standard solution)}/{(the electromotive force of the internal standard solution)−(the electromotive force of the low-concentration standard solution)}.

2. A management system for an electrolyte analyzer comprising:
   ion-selective electrodes to measure concentrations of particular ions in a sample; and
   a balance ratio calculating mechanism for calculating a balance ratio of electromotive forces from an electromotive force of an internal standard solution, an electromotive force of a high-concentration standard solution and an electromotive force of a low-concentration standard solution, all the electromotive forces being obtained from calibration in which a sample of known concentration was measured,
   wherein the balance ratio is calculated from the following equation:
   {(the electromotive force of the high-concentration standard solution)−(the electromotive force of the internal standard solution)}/{(the electromotive force of the internal standard solution)−(the electromotive force of the low-concentration standard solution)}.

3. The management system for an electrolyte analyzer of claim 2, further comprising:
   a fluctuation pattern extracting mechanism for extracting fluctuation patterns of the results of the calibration in which the sample of the known concentration was measured; and
   a comparison mechanism for comparing the fluctuation patterns extracted by the fluctuation pattern extracting mechanism and the fluctuation pattern of the balance ratio obtained by the balance ratio calculating mechanism against atypical patterns stored in advance.

4. The management system for an electrolyte analyzer of claim 3, further comprising:
   a judgment mechanism for judging diluent deterioration based on at least one of the following: an upward drift of a slope measured for chlorine ions, a downward drift of the electromotive force of the internal standard solution measured for chlorine ions, and an upward drift of the balance ratio for chlorine ions,
   wherein all the drifts are obtained from the results of the calibration in which the sample of the known concentration was measured.

5. The management system for an electrolyte analyzer of claim 3, further comprising:
   a judgment mechanism for examining the mixing of foreign substances into a diluent based on at least one of the following: a downward shift of a slope measured for potassium ions, a downward shift of the electromotive force of the internal standard solution measured for potassium ions, an upward shift of the electromotive force of the calibrator measured for potassium ions, and an upward shift of the balance ratio for potassium ions, wherein all the shifts are obtained from the results of the calibration in which the sample of the known concentration was measured.

6. The management system for an electrolyte analyzer of claim 3, further comprising:

a judgment mechanism for judging the deterioration of the ion-selective electrodes based on a downward slope drift in the results of the calibration in which the sample of the known concentration was measured.

7. The management system for an electrolyte analyzer of claim 3, further comprising:

a judgment mechanism for judging error in inputting the concentrations of the standard solutions based on at least one of the following: upward shifts of slopes measured for sodium and chlorine ions, upward shifts of the internal standard solution measured for sodium and chlorine ions, and a downward shift of the internal standard solution measured for potassium ions, wherein all the shifts are obtained from the results of the calibration in which the sample of the known concentration was measured.

8. The management system for an electrolyte analyzer of claim 3, further comprising:

a judgment mechanism for judging the deterioration of a comparative electrode based on at least one of the following: downward drifts of the internal standard solution electromotive forces measured for sodium, potassium, and chlorine ions, downward drifts of the electromotive forces of the high/low-concentration standard solutions measured for sodium, potassium, and chlorine ions, and downward drifts of the electromotive forces of the calibrator measured for sodium, potassium, and chlorine ions, wherein all the drifts are obtained from the results of the calibration in which the sample of the known concentration was measured.

* * * * *